United States Patent [19]

Trivedi et al.

[11] Patent Number: 4,625,813
[45] Date of Patent: Dec. 2, 1986

[54] METHOD AND APPARATUS FOR CORING IN SUBAQUEOUS STRUCTURES

[76] Inventors: Arvind J. Trivedi, 3 Whitehall Way, Englishtown, N.J. 07726; Vincent G. Miller, 235 Benson Pl., Westfield, N.J. 07090

[21] Appl. No.: 745,450

[22] Filed: Jun. 17, 1985

[51] Int. Cl.⁴ ............................................. E21B 10/02
[52] U.S. Cl. ........................................ 175/20; 175/58; 175/244; 175/246; 73/863.85; 73/863.86
[58] Field of Search .................... 175/20, 58, 244, 246, 175/248, 257; 73/863.81, 863.85, 863.86; 166/285

[56] References Cited

U.S. PATENT DOCUMENTS

| | | | |
|---|---|---|---|
| 1,222,249 | 4/1917 | Tuttle . | |
| 2,261,457 | 11/1941 | Wiggins | 220/29 |
| 2,353,530 | 7/1944 | Walker | 210/206 |
| 2,815,663 | 12/1956 | Lupfer | 73/342 |
| 3,007,340 | 11/1961 | Kraftson | 73/432 |
| 3,115,782 | 12/1963 | Echtler, Jr. | 73/422 |
| 3,162,049 | 12/1964 | Blanchard | 73/421 |
| 4,096,754 | 6/1978 | Beveridge, Jr. | 73/432 R |
| 4,294,124 | 10/1981 | Kalwaitis | 73/863.85 |
| 4,350,052 | 9/1982 | Kendall | 73/863.86 |

Primary Examiner—Stephen J. Novosad
Assistant Examiner—William P. Neuder
Attorney, Agent, or Firm—Lee C. Robinson, Jr.

[57] ABSTRACT

Coring of a subaqueous structure having a significant water pressure head on one side is carried out through a full port valve assembly mounted on the inner or dry side of the structure. With the valve open, the barrel of a coring device is inserted, and a core is cut and removed. The valve is closed to prevent inflow of soil and water. The hole from which the core has been removed can be sealed by injecting a grouting compound through the mounted ball valve assembly, or can be injected by means of a mechanical packer. The valve assembly permits coring to be interrupted, for example, to permit rail service operations through a subaqueous railroad tunnel.

21 Claims, 9 Drawing Figures

METHOD AND APPARATUS FOR CORING IN SUBAQUEOUS STRUCTURES

This invention relates to techniques for assessment of the integrity of subaqueous structures, such as railroad or highway tunnels, aqueducts, caissons, dams, etc. In a specific embodiment, the coring method of this invention is employed to monitor and assess the structural integrity of a century-old brick-lined tunnel of the PATH system, that is, the Port Authority Trans-Hudson Rapid Transit Rail System, which crosses under the Hudson River between New York and New Jersey.

The problem to which the method of this invention is addressed can be best seen against the historical background of a particular tunnel, in this case a brick-lined tunnel.

The tunnel in question extends from a shaft in Jersey City, N.J. eastwards towards New York, N.Y. The tunnel was constructed during the period 1874 to 1889, with a generally oval-shaped cross section, approximately 18 feet high and 16 feet wide on the interior, and having, for the most part, a 30-inch-thick brick lining. The tunnel was constructed using a compressed air method to hold back earth and water as the excavation progressed. The excavated portion was then lined with ⅜ inch thick curved boiler plate, over which the brick lining was then installed.

Although attempts had been made to monitor and assess the structural integrity of the brick section of the tunnel, the assessment program was discontinued long ago, and records are scanty concerning the construction and repairs of the tunnel.

After this tunnel was acquired by the PATH System in 1962, a structural integrity program was instituted, including periodic visual inspection of the brick section, periodic settlement surveys, leakage monitoring, and limited out-of-round cross section measurements.

However, these methods have not provided sufficient data concerning the structural integrity of the brick-lined section. It is especially desired to evaluate satisfactorily the brick lined section of the tunnel, in light of the age of that section and its observed condition, so that the PORT AUTHORITY engineering department could evaluate and estimate its remaining service life, and develop a program to ensure its continued useful and safe operation. More specifically, it was necessary to obtain core samples from the brick lined section, but to do so without risk of inrush of wate or materials at any stage of the core sampling process.

Because the core sampling was to be carried out in an active railroad tunnel, it was also necessary that the sampling method be interruptible, and not interfere with normal rapid transit rail operations.

In short, the problem to be solved was to develop a coring method that would supply data concerning the structural integrity of the tunnel, but which would not jeopardize the safety or operations of the rapid transit system. In addition, if the rail operations dictated that coring should be interrupted, the coring method had to permit easy resumption of the coring process.

Accordingly, it is an object of this invention to provide such a coring method, which permits the removal of a core sample from a subaqueous structure.

It is another object of this invention to provide means associated with the method for achieving quick and effective control of water or material leakage.

It is a further object of this invention that the coring method should permit grouting or installation of packer apparatus to repair the cored holes in the subaqueous structure, and to prevent water leakage during grouting.

It is yet another object of this invention that the physical dimensions of the structures associated with this coring apparatus be small enough (where the subaqueous structure is a rail tunnel) to remain outside the clearances required for normal train operations.

According to several preferred embodiments of this invetion, coring is carried out in a subaqueous structure of the type including a wall which has a hydrostatic pressure head on an outer side thereof. To begin with, the inner side of the wall is grouted as necessary to provide a smooth surface, and a port valve assembly is installed on the prepared inner side on the wall. This port valve assembly includes a mounting plate, means anchoring the mounting plate to the inner side of the wall, and a valve having an open position in which a cylindrical bore extends through the valve and a closed position in which the cylindrical bore is blocked. Preferably, a full port floating ball valve is employed. With the port valve assembly mounted on the wall, and with the valve in its open position, the core barrel of a coring device is inserted through the cylindrical bore, a cylindrical core is cut from the wall, and this core is retrieved, thus leaving a generally cylindrical cored hole. When the core barrel and the core are withdrawn through the valve, the valve is closed, thus preventing inflow of water and materials. A grouting device can be installed on the port valve assembly, after which the valve is opened and a grouting compound is installed through the grouting device and the valve assembly into the cored hole. Then, when the grouting compound has set sufficiently, the valve assembly can be removed from the wall.

Instead of mounting or otherwise installing a grouting device on the port valve assembly, a mechanical packer can be inserted into the cored hole. The mechanical packer is generally of the type having a hollow packer stem or tube, an expandable rubber seal which is adjustable to fit the inside of the cored hole, an adjusting nut and sleeve, and a grout valve on the outer side of the packer. The packer itself prevents inflow of water and materials, and can be installed optionally either through the open port valve assembly or, with the port valve assembly removed, directly into the cored hole. Then, a grouting compound is supplied through the packer stem into the cored hole to seal the same. A bleeder tube is usually provided in the mechanical packer for removal of any trapped air and water in the hole for proper grout injection.

In summary, according to the method of this invention, coring is carried out through a fixed gland protruding into the tunnel or other subaqueous structure, the gland being formed of the port valve assembly. The gland is closable to control the inflow of water. The fixed gland also permits grouting of the cored hole through the gland.

The foregoing and many other objects, features, and advantages of this invention will be more fully understood from the ensuing detailed description of preferred embodiments thereof, which is to be considered in connection with the accompanying drawings, in which.

With reference to the drawings, and initially FIGS. 1 and 2 thereof, a prototype coring test run will be described.

In order to simulate the subaqueous structure of the brick-lined tunnel wall, a brick wall of an abandoned warehouse building was selected for a test run. The building had been constructed in the nineteenth century of brick and mortar of the same type as used in the brick lining of the tunnel. Because the warehouse wall was an above-ground structure, it was necessary to simulate the conditions of water and soil inflow both during and after a coring operation.

Figure 1:
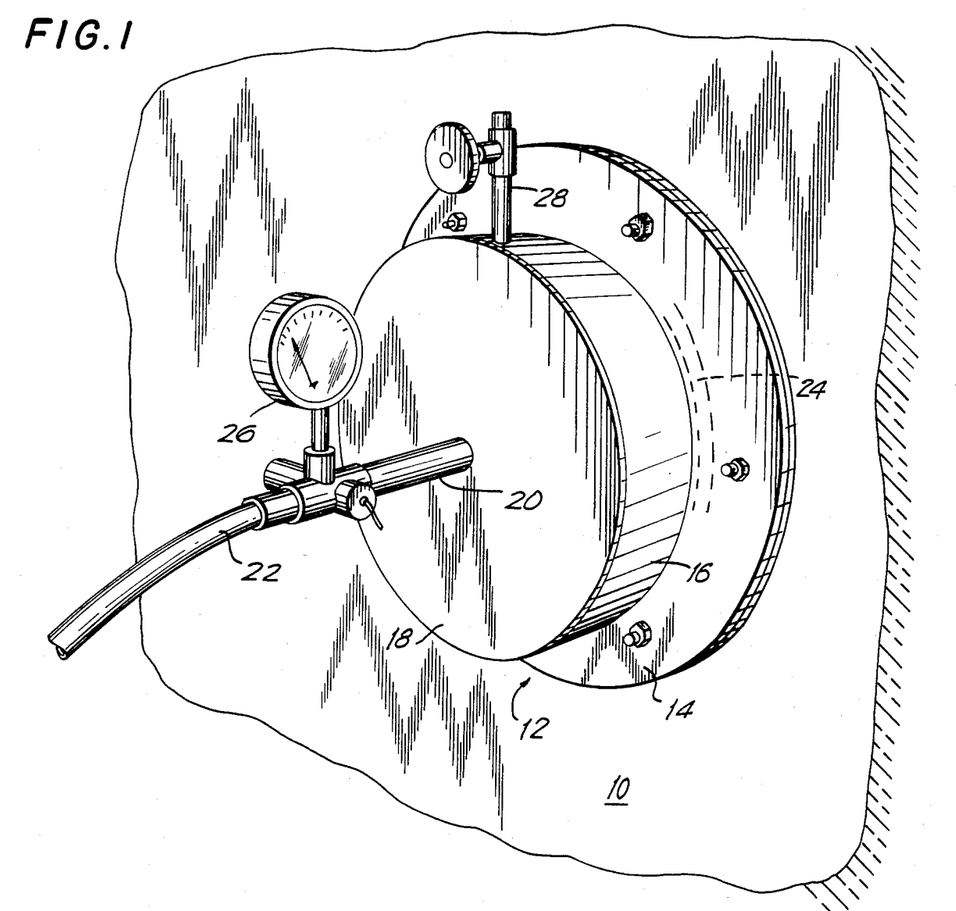
FIG. 1 is a perspective view of a pressure simulator for a test run of the method of this invention.

A hydrostatic head of ninety feet was simulated by installation on one side of the brick wall 10 of a pressure chamber 12, as illustrated in FIG. 1. This chamber 12 is formed of a twenty-six inch diameter flange plate 14 having an eighteen inch central aperture. A six inch long eighteen inch diameter pipe 16 was welded at one end to the flange plate 14, and a circular plate 18 having a one inch diameter central nipple 20 was welded to the other end of the pipe 16. A water pressure hose 22 was connected to the nipple 20. The flange plate 14 was mounted to the wall 10 using suitable anchors sold under the trade name Parabond. In order to minimize leakage during operation, the wall 10 was suitably grouted to cover any irregularities, and a rubber doughnut-shaped seal was employed between the wall 10 and the flange plate 14.

Before installation on the wall, the pressure chamber 12 was provided with a two-inch porous fill of sand and a four inch layer of organic clay to simulate the conditions of soil surrounding the brick section. A filter fabric was employed to separate the sand from the clay and to prevent migration of the sand.

Once mounted on the wall, a hydrostatic head of forty pounds per square inch (equivalent to approximately a ninety foot head of water) was applied through the water pressure hose 22. This pressure was monitored from a gauge 26. A relief valve 28 was also provided on the six inch long pipe 16.

Figure 2:
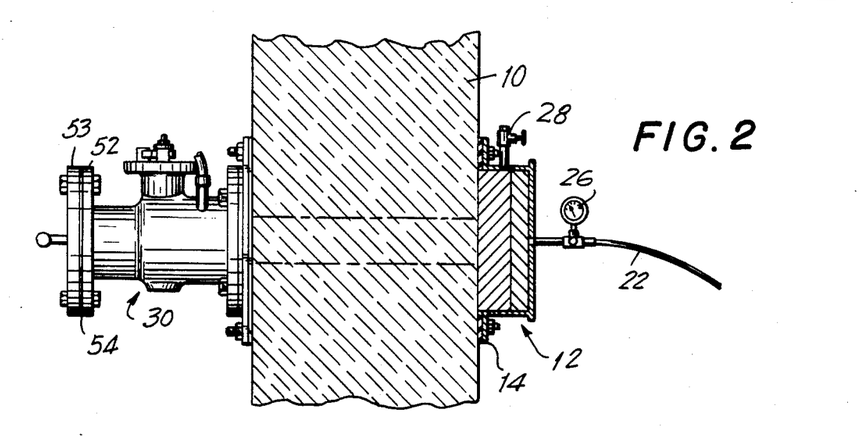
FIG. 2 shows a cross section of a test wall under simulated subaqueous conditions.

As shown in FIG. 2, a port valve assembly 30, to be described in greater detail with reference to FIG. 3, was mounted on the wall 10 opposite the pressure chamber 12, and a coring operation was carried out through the open port valve assembly 30.

Figure 3:
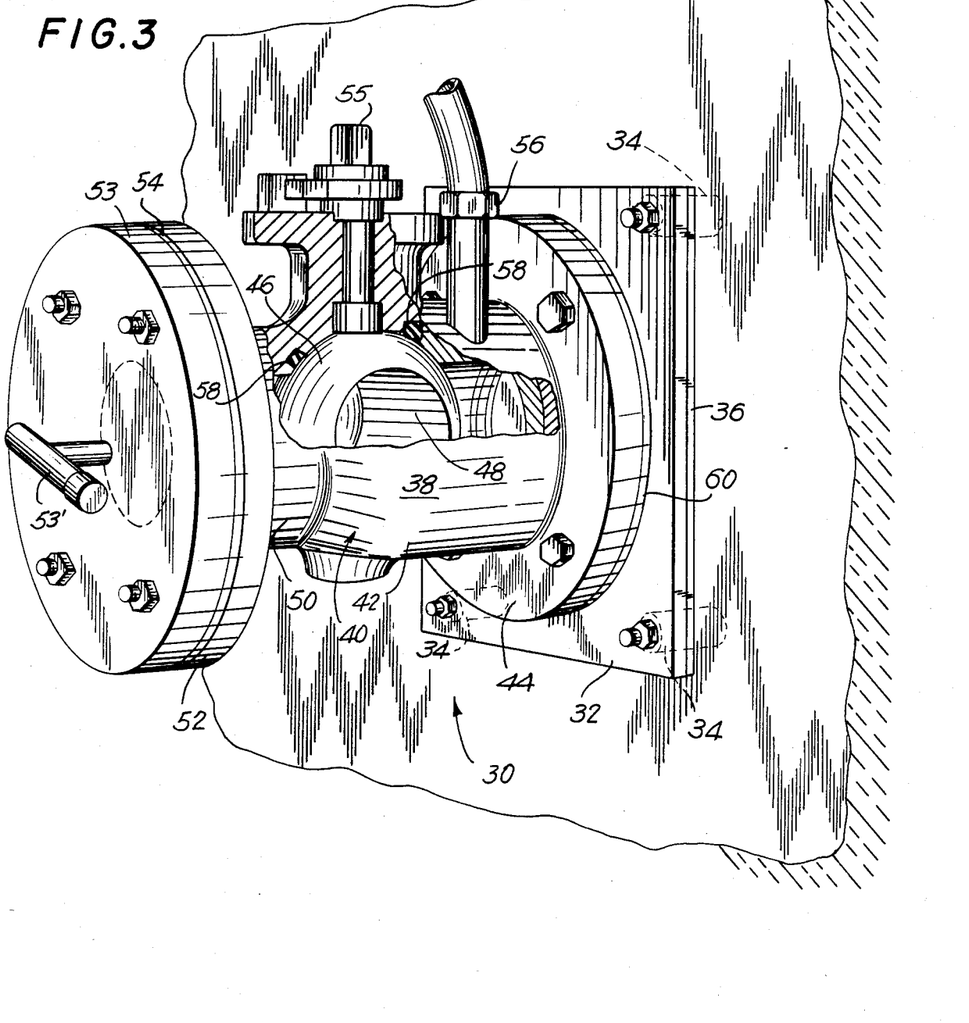
FIG. 3 is a perspective view, partly cut away, showing the port ball valve assembly of this invention.

As shown in FIG. 3, the port valve assembly 30 has an eighteen inch by eighteen inch square steel plate 32, with a 3½ inch hole in its center, to be mounted on the wall 10 on which the core sample is to be taken. Four ¾ inch diameter anchors 34 were placed in the wall 10 for bolting the steel plate 32 to the wall 10. Grout was placed over the wall to provide an even bearing surface, and a doughnut-shaped gasket (not shown) was disposed between the plate 32 and the wall 10.

A four inch diameter full port flanged ball valve 38 was mounted on the steel plate 32. Here, the ball valve 38 was of the type manufactured by Jamesburg Corporation. This full port ball valve 38 has a valve body or housing 40 (see FIG. 8), a first port 42 coupled to a first flange 44 mounted on the plate 32, a floating ball 46 having an opening therethrough of the same diameter as the port 42, a second port 50 facing outward from the plate 32 and an annular flange 52 at the end of the second port 50. A flange plate 53 having a grout plug 53' was removably bolted onto the second flange 52, with a gasket 54 therebetween.

A stem 55 on which a handle could be removably attached was employed for rotating the floating ball 46.

This valve 38 could be opened or closed by rotating the ball 46 through ninety degrees by means of a handle mounted on the stem 55. With the ball in its open position, that is, with the ball opening 48 aligned with the ports 42 and 50, a four inch diameter bore extends through the valve 38 and the plate 32 to the wall 10. If the handle is rotated through 90 degrees, the ball 46 permits quick shut off and seals the passage through the valve 38.

An optional wash outlet 56 was affixed onto the valve housing 40.

Here, circular seals 58 are shown disposed between the body of the valve 38 and the ball 46, the seals 58 being disposed about the respective ports 42 and 50 and sealingly biased against the ball 46.

A gasket 60 seals the flange 44 to the plate 32.

The ball valve assembly 30 of FIG. 3 easily fits within a 14 inch maximum clearance from the wall 10. Thus, when appropriately located, the valve assembly 30 can be left in place in the tunnel, if required, permitting disruption of coring and resumption of train operations, and, because of its small lengthwise dimension, the assembly 30 would pose no clearance problems.

Figure 4:
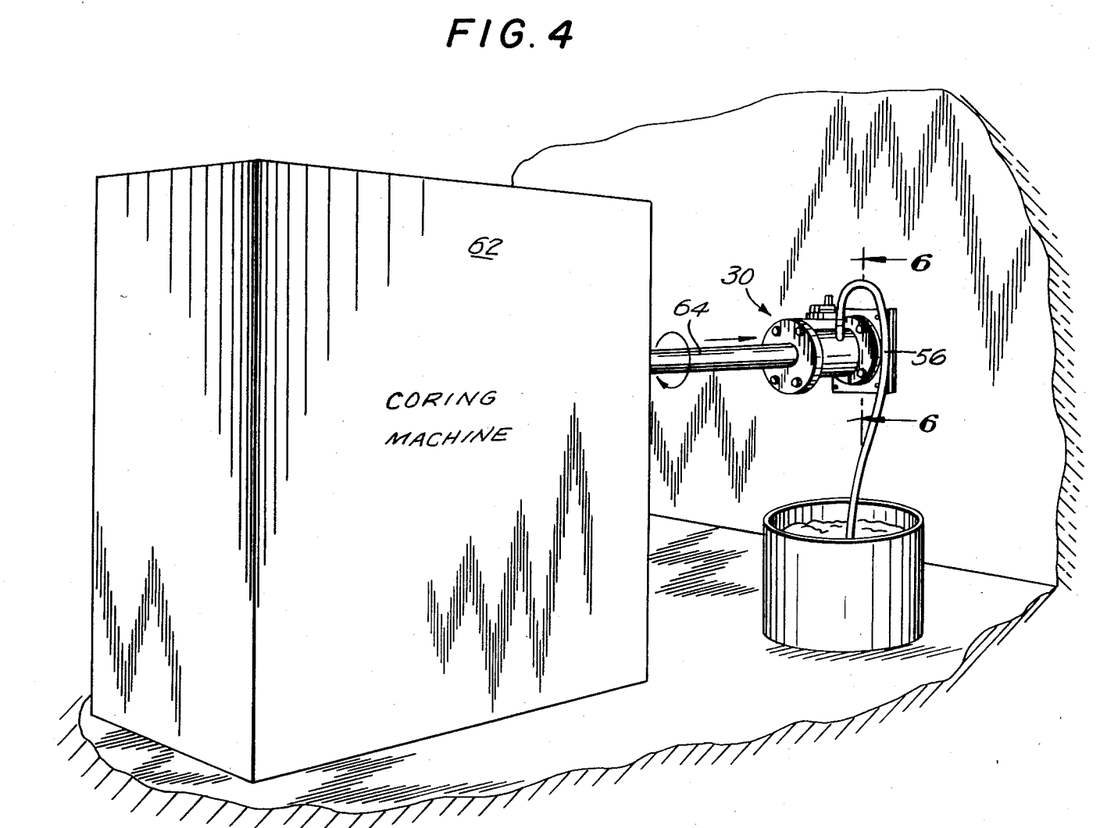
FIG. 4 is a perspective view showing a coring operation being carried out through the port ball valve assembly in accordance with this invention.

As shown in FIG. 4, the coring of the wall is carried out by use of a coring machine or drilling rig 62. A hollow core barrel 64 having a diamond tip coring bit 66 (FIG. 5) was inserted into the open ball valve assembly 30, and the core barrel 64 was rotated. Water was circulated through the bit 66 under pressure to cool the bit and to remove the cuttings. In the test run operation, the wash water flowed out through the wash outlet 56 to a disposal vat.

When the wall was penetrated, the core barrel was partially retracted, and the valve handle was attached. The ball valve 38 was closed as the core barrel 64 was completely retracted. Here, the ball valve 38 was completely effective to stop inflow of soil and water.

The grouting plate 53 was bolted to the valve flange 52, and a cement grout was pumped under pressure through the grout plug 53'. After the grout had set, the ball valve was removed. No further leakage occurred through the hole.

During this coring operation, coring was suspended after each successive one foot penetration, the core barrel retracted, and the ball valve closed. No leakage was encountered during any of these one-foot stages of the coring operation.

After the success of the test run, a coring operation was attempted in the rail tunnel. A description follows of the technique employed for in-tunnel coring.

Figure 5:
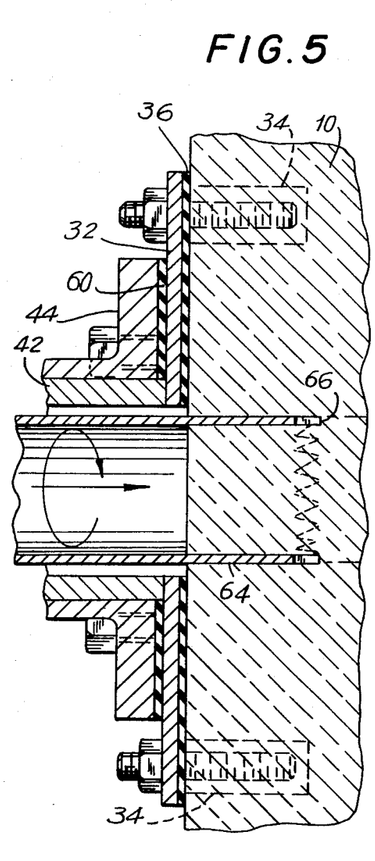
FIG. 5 is a cross section of a portion of the coring apparatus of this invention.
Figure 6:
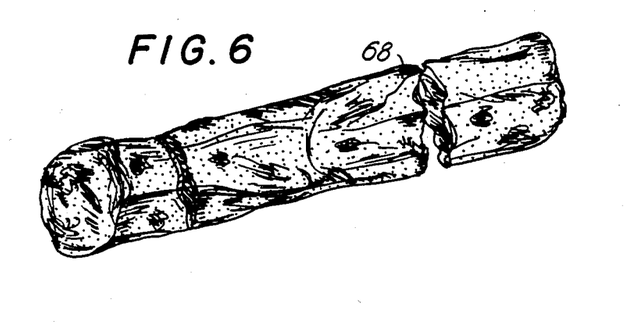
FIG. 6 illustrates a core as retrieved from a subaqueous structure.
Figure 7:
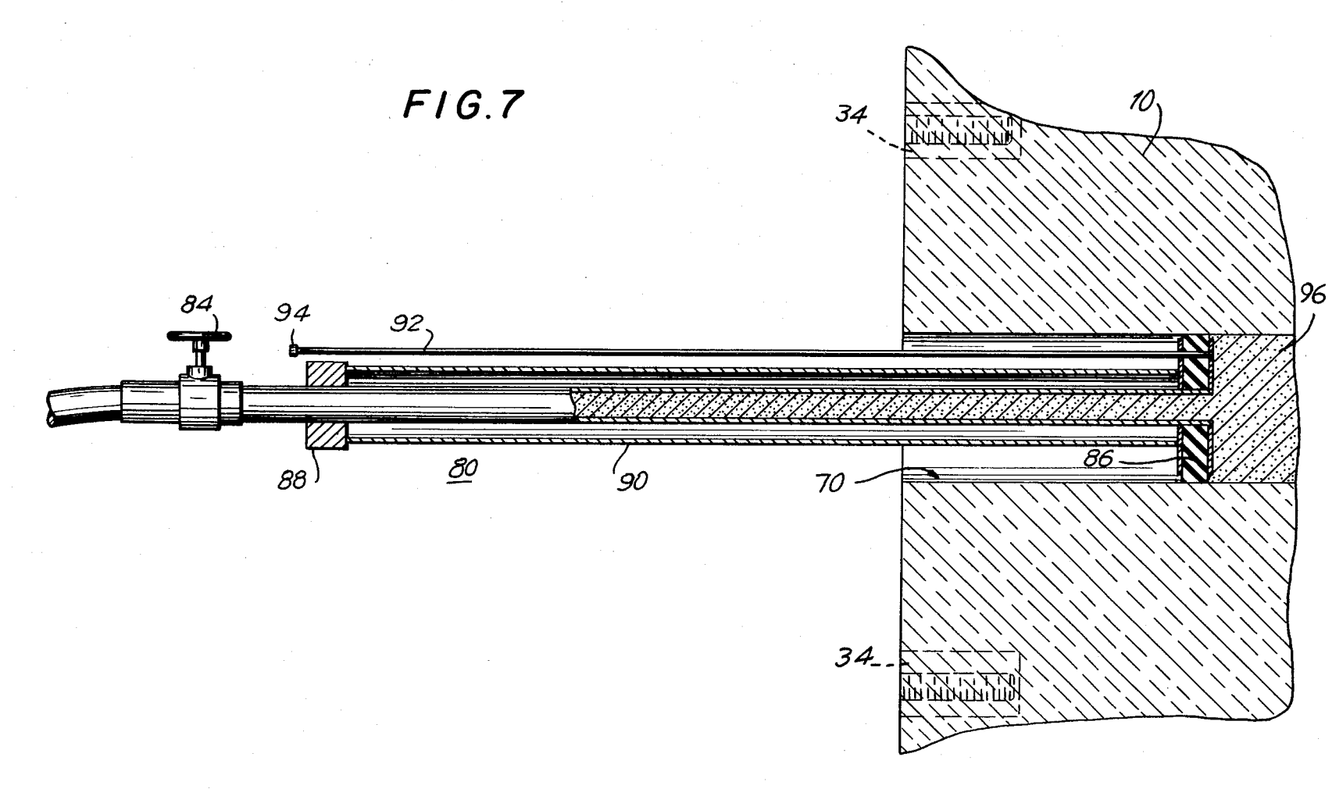
FIGS. 7 and 8 illustrate alternative modes of employment of a mechanical packer in connection with this invention.

In the coring of the brick-lined tunnel, the ball valve assembly 30 is installed on the wall 10 with a one-inch thick doughnut-shaped seal (not shown) between the wall 10 and the mounting plate 32. A pneumatically powered drilling rig mounted on a flat car can be favorably employed for core drilling, with the drilling being carried out in the same general fashion as shown in FIGS. 4 and 5. Cores of 3 feet to 4 feet in length, of which an example 68 is shown in FIG. 6, can be taken through the brick lining, and any other layers, up to the steel boiler plate of the tunnel wall, leaving a generally cylindrical cored hole 70 (FIG. 7). Then, the core is logged, and the hole is grouted, either by applying a cement grout through the grout plate 35' or, alternatively, by employing a mechanical packer, as described in connection with FIGS. 7 and 8.

Figures 8, 9:
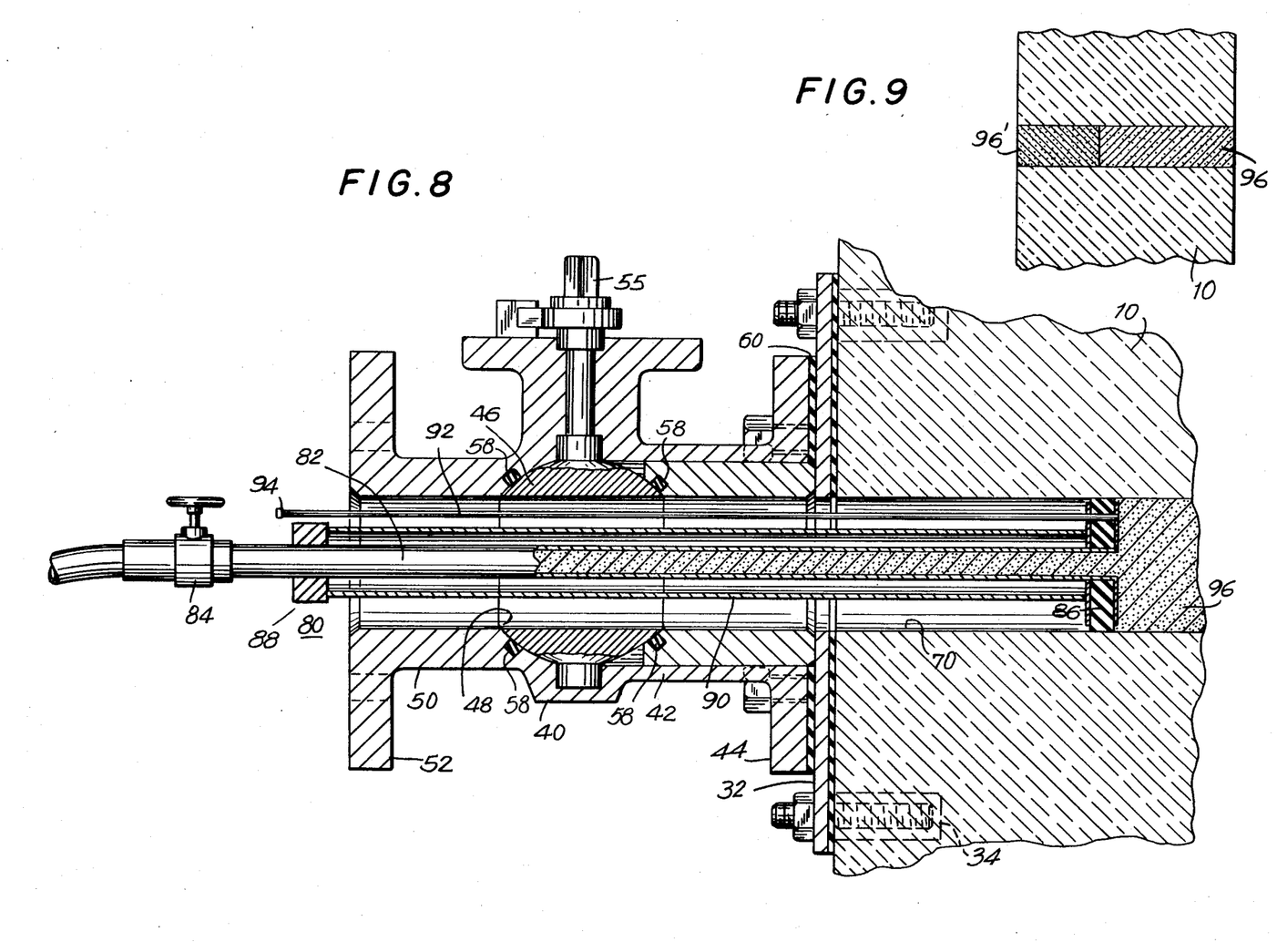
FIG. 9 is a cross sectional view of a subaqueous structure that has been cored and grouted.

A mechanical packer can be favorably employed to control leakage through a hole 70. In this case, the mechanical packer 80 comprises a hollow metal tube or stem 82 with a grout vae 84 disposed at its proximal end and a mechanically expandable rubber plug 86 at its distal end. An adjusting nut 88 tightens or loosens an associated adjustment sleeve 90 for expanding or contracting the rubber plug 86 against the wall of the cored hole 70. A bleeder tube 92 with a cap 94 is provided for removal or any trapped air and water in the hole 70 for proper grout injection.

Where the water inflow through the cored hole 70 is tolerably low, for example, 5 GPM or less, the ball valve assembly 30 can be removed from the wall, and the mechanical packer will be sufficient to prevent inflow of water. Then, a grouting hose is connected to the grout valve 84, and a grouting compound 96 is injected through the mechanical packer 80 into the cored hole 70. Air and water from the cored hole 70 is permitted to esape through the bleeder tube 92.

Where required, the mechanical packer can be employed through the mounted ball valve assembly 30, as illustrated in FIG. 8.

After the grouting compound 96 has set sufficiently, the mechanical packer 80 is removed from the cored hole 70. Then, an additional grout 96' can be injected to finish the hole 70, as shown in FIG. 9.

In a preferred technique, cement silicate grout is first injected through the mechanical packer 80. Then the packer 80 is removed and a chemical acrylamide grout is injected, completely sealing the cored hole 70.

With the four inch diameter bore of the ball valve assembly 30, a core of any size up to about $3\frac{5}{8}$ inch diameter can be taken. However, a core of smaller diameter can also be taken.

The anchors 34 can be of the type having a threaded rod stud and a sealed glass capsule containing a premeasured amount of a polyester resin or other systems unaffected by water or corrosives, together with sand aggregate and a hardener. However, expansion anchors also perform satisfactorily for most coring operations.

The coring technique of this invention permits excellent retrieval of core samples from subaqueous structures subject to a significant hydrostatic head, without risk of inflow of material and water. The technique further permits the secure sealing of the resulting cored holes, employing conventional grouting compounds.

Of course, the technique of this invention is not limited to the analysis of brick wls for railroad tunnels, but can be employed anywhere that there is a significant pressure head on one side of a structural member to be analyzed.

For the sake of convenience, the term "outer" has been employed to refer to the side of the structure that has a hydrostatic pressure head, and the term "inner" has been used to refer to the side at a lower pressure. These terms are to be interpreted liberally, to suit the subaqueous structure in need of analysis. For example, while the outer and inner sides of a tunnel river crossing would have the sense of outer and inner referred to above, in the case of an aqueduct where the water under pressure is inside, senses of these terms should be reversed.

While a full port floating ball valve has been shown in the preferred embodiment, it should be understood that the valve can take on other forms, so long as the valve, in its open position, provides a generally cylindrical bore extending through the valve to the structure to be cored. For example, such a valve could be a slide valve or gate valve.

Furthermore, while preferred embodiments of this invention have been described in detail hereinabove, it should be understood that the invention is not limited to those embodiments, and that many modifications and variations thereof would suggest themselves to those of skill in the art without departure from the scope and spirit of this invention, as defined in the appended claims.

What is claimed is:

1. A method of coring in a subaqueous structure including a wall having a hydrostatic pressure head on an outer side thereof, comprising:
   installing on an inner side of said wall a port valve assembly including a mounting plate, means anchoring the mounting plate to the inner side of said wall, and a valve having an open nosition in which a cylindrical bore extends through the valve and a closed position in which the cylindrical bore is blocked;
   with said valve in its open position, inserting a coring device through said cylindrical bore, cutting a cylindrical core of said wall, and retrieving said core thus leaving a generally cylindrical cored hole;
   placing the valve into its closed position;
   installing a grouting device on said port valve assembly;
   placing said valve into its open position;
   installing grouting compound through said grouting device into said cored hole; and
   removing said valve assembly.

2. A method of coring in a subaqueous structure including a wall having a hydrostatic pressure head on an outer side thereof, comprising:
   installing on an inner side of said wall a port valve assembly including a mounting plate having a circular aperture, means anchoring the mounting plate to the inner side of said wall, sealing means disposed between said mounting pate and said wall about said circular aperture, and a valve having an open position in which a cylindical bore extends through the valve and mounting plate and a closed position in which the cylindrical bore is blocked;
   with said valve in its open position, inserting a coring device through said cylindrical bore, cutting a cylindrical core of said wall, and retrieving said core thus leaving a generally cylindrical cored hole;
   placing the valve into its closed position;
   installing a grouting device on said port valve assembly;
   placing the valve into its open position;
   installing grouting compound through said grouting device into said cored hole; and
   removing said port valve assembly.

3. A method of coring in a subaqueous structure including a wall having a hydrostatic pressure head on an outer side thereof, comprising:

installing on an inner side of said wall a port valve assembly including a mounting plate, means anchoring the mounting plate to the inner side of said wall, and a ball valve having a ball member rotatable between open and closed positions, wherein in its open position a cylindrical bore extends through the valve and the mounting plate to the wall;

with said valve in its open position, inserting a coring device through said cylindrical bore, cutting a cylindrical core of said wall, and retrieving said core thus leaving a generally cylindrical cored hole;

placing the valve into its closed position;

installing a grouting device on said port valve assembly;

placing said valve into its open position;

installing grouting compound through said grouting device into said cored hole; and removing said valve assembly.

4. A method of coring in a subaqueous structure including a wall having a hydrostatic pressure head on an outer side thereof, comprising:

installing on an inner side of said wall a port valve assembly including a mounting plate, means anchoring the mounting plate to the inner side of said wall, and a ball valve including a housing having a cylindrical inlet and a cylindrical outlet, and a ball member within said housing rotatable between the open and closed positions wherein in its open position a cylindrical bore extends through said inlet, said ball member and said outlet, and a pair of sealing rings disposed in said housing about said inlet and outlet and sealingly biased against said ball member;

with said valve in its open position, inserting a coring device through said cylindrical bore, cutting a cylindrical core of said wall, and retrieving said core thus leaving a generally cylindrical cored hole;

placing the valve into its closed position;

installing a grouting device on said port valve assembly;

placing said valve into its open position;

installing grouting compound through said grouting device into said cored hole; and removing said valve assembly from said wall.

5. A method of coring as defined in claim 4, wherein the installing of the port valve assembly includes installing a sealing gland between said mounting plate and said wall.

6. A method of coring in a subaqueous structure including a wall having a hydrostatic pressure head on an outer side thereof, comprising:

installing on an inner side of said wall port valve assembly including a mounting plate, means anchoring the mounting plate to the inner side of said wall, and a valve having an open position in which a cylindrical bore extends through the valve and a closed position in which the cylindrical bore is blocked;

with said valve in its open position, inserting a coring deivce through said cylindrical bore, cutting a cylindrical core of said wall, and retrieving said core thus leaving a generally cylindrical cored hole;

placing the valve into its closed position;

installing in said valve a mechanical grouting packing;

placing said valve into its open position;

installing grouting compound through said mechanical packer into said cored hole;

removing said mechanical packer; and removing said valve assembly.

7. A method of coring in a subaqueous structure including a wall having a hydrostatic pressure head on an outer side thereof, comprising:

installing on an inner side of said wall a port valve assembly including a mounting plate, means anchoring the mounting olate to the inner side of said wall, and a valve having an open position in which a cylindrical bore extends through the valve and a closed position in which the cylindrical bore is blocked;

with said valve in its open position, inserting a coring device through said cylindrical bore, cutting a cylindrical core of said wall, and retrieving said core thus leaving a generally cylindrical cored hole;

installing through said valve and into said cored hole a mechanical grouting packer having a hollow packer stem, a grout valve at a proximal end of said stem, an expandable plug at a distal end of the stem, mean for expanding said plug, and a bleeder tube extending through said plug;

expanding said plug;

injecting a suitable grouting compound through said grout valve and packer stem into said cored hole while removing any trapped air and water from the hole through the bleeder tube;

removing said mehcanical packer; and removing said valve assembly from said wall.

8. A method of coring as defined in claim 7, wherein said injecting includes first injecting a cement grout and then injecting a waterproof hydraulic grout.

9. A method of coring in a subaqueous structure including a wall having a hydrostatic pressure head on an outer side thereof, comprising:

installing on an inner side of said wall a port valve assembly incluidng a mounting plate, means anchoring the mounting plate to the inner side of said wall, and a ball valve including a housing having first and second cylindrial ports aligned with one another and a rotatable ball member having a cylindrical passage therethrough and disposed within said housing and rotatable between open and closed positions, with the first port being mounted to said mounting plate, wherein said open position a cylindrical bore extends through said ports and ball member to said wall, and further including a wash discharge outlet in one of said first and second ports communicating with said cylindrical bore;

with said valve in its open position, inserting a coring device through said cylindrical bore, cutting a cylindrical core of said wall while supplying a wash through said device and removing the wash through said wash discharge outlet, and retrieving said core thus leaving a generally cylindrical cored hole;

placing the valve into its closed position;

installing in said second port a grouting device;

placing said valve into its open position;

injecting a suitable grouting compound through said grouting device into said cored hole; and removing said valve assembly.

10. A method of coring in a subaqueous structure including a wall having a hydrostatic pressure head on an outer side thereof, comprising:

installing on an inner side of said wall a port valve assembly including a mounting plate, means anchoring the mounting plate to the inner side of said wall, and a valve having an open position in which a cylindrical bore extends through the valve and a closed position in which the cylindrical bore is blocked;

with said valve in its open position, inserting a coring device through said cylindrical bore, cutting a cylindrical core of said wall, and retrieving said core thus leaving a generally cylindrical core hole;

placing the valve into its closed position;

installing a grouting nipple on a proximal end of said valve;

placing said valve into its open position;

injecting a grouting compound through said grouting nipple and said cylindrical bore into said cored hole; and removing said port valve assembly.

11. A method of coring in a subaqueous structure including a wall having a hydrostatic pressure head on an outer side thereof, comprising installing on an inner side of said wall a port valve assembly including a mounting plate, means anchoring the mounting plate to the inner side of said wall, and a valve having an open position in which a cylindrical bore extends through the valve and a closed position in which the cylindrical bore is blocked;

with said valve in its open position, inserting a coring device through said cylindrical bore, cutting a cylindrical core of said wall, and retrieving said core thus leaving a generally cylindrical cored hole;

installing a mechanical grouting packer into said cored hole;

installing a grouting compound through said packer into said cored hole; and removing said mechanical packer after said grouting compound has set sufficiently.

12. A method of coring as defined in claim 11, wherein said valve assembly is removed from said wall before installing the mechanical packer into said cored hole.

13. A method of coring as defined in claim 11, wherein said coring is carried out in stages throughout the thickness of said wall, the cylindrical core is retrieved as core portions for the respective stages prior to coring for the next successive stages; and further comprising closing said valve when each successive core portion is retrieved.

14. A method of coring in a subaqueous structure including a wall having a hydrostatic pressure head on an outer side thereof, comprising installing on an inner side of said wall a port valve assembly including a mounting plate, means anchoring the mounting plate to the inner side of said wall, and a valve having an open position in which a cylindrical bore extends through the valve and a closed position in which the cylindrical bore is blocked;

with said valve in its open position, inserting a coring device through said cylindrical bore, cutting a cylindrical core of said wall, and retrieving said core thus leaving a generally cylindrical cored hole; and installing a grouting compound into said cylindrical cored hole to seal the same.

15. A method of coring as defined in claim 14, wherein said coring device has a rotary hollow core barrel whose outside diameter is less than the inside diameter of the bore of said valve.

16. A method of coring in a subaqueous structure including a wall having a hydrostatic pressure head on an outer side thereof, comprising:

applying grout to an inner side of said wall to form an even bearing surface;

installing on said wall over said even bearing surface a port valve assembly including a mounting plate bearing against said even bearing surface, means anchoring the mounting plate to the inner side of said wall, and a valve having an open position in which a generally cylindrical bore extends through the valve and a closed position in which the cylindrical bore is blocked;

with said valve in its open position, inserting a coring device through said cylindrical bore, cutting a cylindrical core of said wall, and retrieving said core thus leaving a generally cylindrical cored hole;

installing grouting compound into said cored hole to seal the same; and removing said valve assembly from said wall.

17. A method of coring in a subaqueous structure including a wall having a hydrostatic pressure head on an outer side thereof, comprising:

installing on an inner side of said wall a port valve assembly including a mounting plate; means anchoring the mounting plate to the inner side of said wall, and a valve having an open position in which a cylindrical bore extends through the valve and a closed position in which the cylindrical bore is blocked;

with the valve in its open position, inserting a coring device through said cylindrical bore, boring partway through said wall thus cutting a cylindrical core of said wall, and retrieving said core, thus leaving a generally cylindrical cored hole in said wall;

placing said valve in its closed position;

resuming coring of said wall by opening said valve, reinserting said coring device, cutting a further cylindrical core of said wall, and removing the further core thus lengthening said cored hole;

installing grouting compound into said cored hole; and removing said valve assembly.

18. A port valve assembly for extraction of core samples from a subaqueous structure and subsequent grouting of the resulting cored hole in said structure, comprising a flanged full port ball valve having a valve body with first and second flanges and a rotatable ball having an opening therein wherein in an open position a generally cylindrical bore extends through the valve from said first flange through the ball opening to said second flange, and in a closed position with said ball rotated substantially 90° said bore is blocked shut; a mounting plate having a circular hole aligned with said cylindrical bore, said second flange being mounted on said mounting plate; and sealing means carried by said valve body for introducing grouting material through said bore and into the cored hole in the subaqueous structure to thereby seal said hole.

19. A port valve assembly according to claim 18, in which the sealing means comprises a flanged plate and a grouting plug thereon, said flanged plate being mounted on the first flange of said ball valve body.

20. A port valve assembly according to claim 18, wherein the bore of said ball valve is substantially 4 inches in diameter, and said port valve assembly has a maximum length, taken in the direction of said bore, of less than 14 inches, thereby permitting cutting and retrieval of up to $3\frac{5}{8}''$ diameter.

21. A port valve assembly according to claim 18, further comprising a plurality of anchors for holding said mounting plate securely against the surface of a subaqueous structure to be cored.

* * * * *